United States Patent
Cox et al.

(10) Patent No.: US 9,545,255 B2
(45) Date of Patent: *Jan. 17, 2017

(54) METHODS AND APPARATUS FOR REVISION OF OBESITY PROCEDURES

(71) Applicant: USGI Medical, Inc., San Clemente, CA (US)

(72) Inventors: John A. Cox, San Clemente, CA (US); Tracy Maahs, San Clemente, CA (US); Richard C. Ewers, San Clemente, CA (US); Eugene Chen, San Clemente, CA (US); Cang Lam, San Clemente, CA (US); Lee Swanstrom, San Clemente, CA (US)

(73) Assignee: USGI Medical, Inc., San Clemente, CA (US)

( * ) Notice: Subject to any disclaimer, the term of this patent is extended or adjusted under 35 U.S.C. 154(b) by 51 days.

This patent is subject to a terminal disclaimer.

(21) Appl. No.: 14/282,396

(22) Filed: May 20, 2014

(65) Prior Publication Data

US 2014/0257351 A1 Sep. 11, 2014

Related U.S. Application Data

(63) Continuation of application No. 11/342,288, filed on Jan. 27, 2006, now Pat. No. 8,726,909.

(51) Int. Cl.
*A61B 17/11* (2006.01)
*A61B 17/29* (2006.01)
(Continued)

(52) U.S. Cl.
CPC ............ *A61B 17/1114* (2013.01); *A61B 17/29* (2013.01); *A61F 5/0083* (2013.01);
(Continued)

(58) Field of Classification Search
CPC .................... A61B 17/1114; A61B 2017/1117; A61B 17/29; A61B 2017/0417; A61B 2017/0419; A61B 2017/1103; A61B 2017/1125; A61F 5/0083; A61F 5/0086
See application file for complete search history.

(56) References Cited

U.S. PATENT DOCUMENTS 7,520,884 B2  4/2009  Swanstrom et al.
7,704,264 B2  4/2010  Ewers et al.
(Continued)

*Primary Examiner* — Andrew Iwamaye
(74) *Attorney, Agent, or Firm* — Kenneth H. Ohriner; Perkins Coie LLP

(57) ABSTRACT

Methods and apparatus for the endoluminal revision of previously performed obesity procedures which have failed are described. One or more endoluminal instruments may be advanced per-orally into the previously formed failed pouch where a number of different procedures can be performed. One or more tissue folds can be formed and secured to reduce the size of the pouch, or the stoma connecting the pouch to the intestinal tract can be reduced in size using endoluminally deployed tissue anchors. These procedures can be performed entirely from within the pouch lumen or upon the exterior surface of the pouch via transgastric entry of the instruments into the peritoneal cavity of a patient. Alternatively, the interior tissue within the pouch can be injured or sclerosed to shrink the pouch lumen. In another alternative, a length of the Roux limb can be shortened endoluminally to create a malabsorptive region.

18 Claims, 21 Drawing Sheets

(51) Int. Cl.
    *A61B 17/04*        (2006.01)
    *A61F 5/00*         (2006.01)
    *A61B 17/00*        (2006.01)

(52) U.S. Cl.
    CPC ............ *A61B 2017/00278* (2013.01); *A61B 2017/00349* (2013.01); *A61B 2017/0417* (2013.01); *A61B 2017/0419* (2013.01); *A61B 2017/1103* (2013.01); *A61B 2017/1125* (2013.01); *A61B 2017/1142* (2013.01); *A61B 2017/2905* (2013.01); *A61F 5/0086* (2013.01)

(56) References Cited

U.S. PATENT DOCUMENTS

| | | |
|---|---|---|
| 7,918,869 B2 | 4/2011 | Saadat et al. |
| 8,088,132 B2 * | 1/2012 | Roslin ............. 606/153 |
| 8,216,252 B2 | 7/2012 | Vaughan et al. |
| 8,726,909 B2 | 5/2014 | Cox et al. |
| 2004/0162568 A1 * | 8/2004 | Saadat et al. ........... 606/139 |
| 2004/0215216 A1 * | 10/2004 | Gannoe et al. ............. 606/151 |
| 2004/0225305 A1 * | 11/2004 | Ewers ............... A61B 1/00135 606/153 |
| 2005/0251165 A1 | 11/2005 | Vaughan et al. |
| 2005/0251176 A1 * | 11/2005 | Swanstrom ......... A61B 1/0014 606/153 |
| 2006/0135971 A1 * | 6/2006 | Swanstrom ......... A61B 1/0014 606/153 |
| 2007/0208360 A1 * | 9/2007 | Demarais et al. ............ 606/153 |

\* cited by examiner

METHODS AND APPARATUS FOR REVISION OF OBESITY PROCEDURES

PRIORITY CLAIM

This application is a Continuation of U.S. patent application Ser. No. 11/342,288, filed Jan. 27, 2006, now pending and incorporated herein by reference.

The present invention relates to methods and apparatus for the revision of obesity-related surgical procedures. More particularly, the present invention relates to the revision and/or correction of surgically altered anatomy within a patient body which has been surgically altered for the treatment of morbid obesity. The methods and apparatus utilize endoluminal procedures and instruments.

BACKGROUND OF THE INVENTION

Generally, three types of bariatric procedures are typically performed on patients for the treatment of morbid obesity. The various surgical procedures include vertical banded gastroplasty ("VBG"), laparoscopic gastric banding ("Lap-Band"), and the Roux-en-Y gastric bypass ("RYGB").

The RYGB procedure is a complex surgical procedure in which a small upper pouch P is created by stapling the stomach S and separating the pouch P from the remaining stomach S, which is left in place in the patient body. A Y-shaped segment of the intestines I (Roux limb), such as the upper jejunum JE or ilium IL, is rerouted and attached to the newly created pouch P via an anastomosis PA, as shown in FIG. 1A. The remaining portion of the jejunum JE is then reattached to the Roux limb at a lower point via an anastomosis IA. This rerouting causes food to pass through the esophagus E, through the pouch anastomosis PA, and into the Roux limb to bypass the stomach S. The pouch P further restricts the food intake and interferes with absorption to result in consistent weight loss.

In creating a VBG, a surgical stapler is used to form a staple line SL to create a small gastric pouch out of the stomach S just below the esophagus E. A non-adjustable polypropylene mesh band B is placed around the bottom of the pouch and through a circular window W created through the stomach S to restrict the size of its outlet, as shown in FIG. 1B. The small pouch and narrow outlet restricts the amount of food the patient can comfortably consume and delays the emptying of food into the remaining portion of the stomach S and duodenum DU.

However, in these types of surgical procedures, there is typically a failure rate of about 20% which is categorized into two types: acute and chronic failures. Acute failures are generally due to patient intolerance, leaks from either the pouch P or anastomoses PA and/or IA, and other complications. Chronic failures generally occur in about 10-20% of patients who fail to lose any significant amount of weight. The typical two failure modes occur from either (1) dilation of the pouch P, for example, where the pouch P expands from a 20-30 cc pouch to a 100-300 cc pouch; or from (2) dilation of the stoma through the pouch anastomosis PA, for example, where the stoma dilates from a 10-12 mm diameter to a 3-5 cm diameter.

Options for correcting these failures are limited to either simply leaving the dilated tissue or to perform an open surgical revision procedure to alter the length of the Roux limb to decrease absorption. However, such a procedure is typically accompanied by a 2-5% mortality rate and a 50% failure rate and is extremely difficult to perform due to the altered tissue anatomy. Moreover, minimally invasive laparoscopic surgical revision procedures are also extremely difficult because of the altered tissue anatomy and scar tissue.

Accordingly, in view of the foregoing, it would be desirable to provide minimally invasive methods and apparatus for performing endoluminal revision procedures to correct failed surgical procedures for obesity.

BRIEF SUMMARY OF THE INVENTION

Correction of failed obesity procedures in a minimally invasive manner may involve a number of different methods and instruments. The instruments may be introduced transgastrically, percutaneously, etc., into the patient's body and into or around a failed pouch previously created through a surgical procedure such as a RYGB, VBG, etc. Once the instruments are positioned within or adjacent to the pouch, tissue within or from the pouch may be temporarily engaged or grasped and the engaged tissue may be manipulated by a surgeon or practitioner from outside the patient's body.

In engaging, manipulating, and/or securing the tissue, various methods and devices may be implemented. For instance, tissue securement devices may be delivered and positioned via an endoscopic apparatus for contacting a tissue wall of the pouch lumen, creating one or more tissue folds, and deploying one or more tissue anchors through the tissue fold(s). The tissue anchor(s) may be disposed through the muscularis and/or serosa layers of the pouch lumen. A shape-lockable or rigidizable endoscopic assembly having an elongate body, a steerable distal portion, and multiple lumens defined therethrough may be advanced into a pouch per-orally and through the esophagus. A tissue manipulation assembly positioned at the distal end of a tubular body may be passed through the endoscopic assembly for engaging and securing the tissue.

Utilizing one or more of the instruments, the rigidizable endoscopic body may be used to pass the flexible body therethrough and into the pouch where it may be used to approximate folds of tissue which are secured via expandable tissue anchors expelled from the tissue manipulation assembly. Any number of tissue folds, i.e., one or more, may be created in a uniform pattern or randomly throughout the pouch lumen such that the enlarged pouch is reduced in size to a pouch having a smaller volume.

The instruments may be utilized endoluminally entirely within the pouch or transgastrically, where one or more tissue ridges may be formed from an exterior surface of the pouch. In this case, a transgastric opening may be created through the pouch to allow for passage of the instruments into the peritoneal cavity.

Another method may include reducing a diameter of the stoma between the pouch lumen and the intestinal tract through the pouch anastomosis. The tissue manipulation assembly may be directed to the tissue circumferentially around the anastomotic connection where one or several pairs of tissue anchors may be deployed into the tissue randomly or in a uniformly spaced configuration around the pouch anastomosis to reduce the opening to a smaller anastomosis which is more effective in restricting the passage of food received within the pouch lumen.

Another method may utilize an endoluminal tissue ablation instrument, e.g., plasma torch, laser, radio-frequency probe, etc., to ablate one or more regions of tissue within the pouch to shrink the tissue and ultimately shrink the size of the pouch.

To facilitate the grasping and manipulation of the tissue within the pouch, various methods and instruments may be utilized. In one example, a tissue engagement member may be positioned through the elongate body and utilized with the tissue manipulation assembly. In another example, the tissue manipulation assembly may be positioned within the pouch lumen with the lower and upper jaw members positioned in an open configuration for receiving tissue therebetween. The air, along with any other fluids, contained within the pouch lumen may be evacuated out, e.g., through one of the lumens defined through the elongate body or through a catheter advanced through the body. The evacuation of air and fluids from the pouch lumen may collapse the pouch tissue onto the flexible body and between the jaw members.

In yet another example, a Verres needle may be advanced percutaneously and positioned through the abdominal wall of a patient. A gas (e.g., air, carbon dioxide, nitrogen, etc.) may be pumped into the peritoneal cavity of the patient body to collapse the tissue of the pouch onto and over the tissue manipulation assembly, particularly between the jaw members positioned within the pouch lumen. The collapsed pouch tissue positioned between the jaw members may then be easily grasped and secured by deploying one or more tissue anchors through the collapsed pouch tissue.

In yet another method for facilitating engagement of the interior tissue, an elongate laparoscopic instrument having a blunted atraumatic tip may be advanced through a percutaneous opening and into contact with an outer surface of the pouch. Once the atraumatic tip contacts the outer surface of the pouch, the laparoscopic instrument may be pushed against the outer surface such that a fold of tissue is formed within the pouch lumen in the proximity of the tissue manipulation assembly. With the tissue fold formed within the pouch lumen, the jaw members of the tissue manipulation assembly may be positioned on either side of the tissue fold to grasp and secure the tissue. Once the tissue fold has been secured, the laparoscopic instrument may be repositioned at another location on the outer surface of the pouch.

In endoluminally revising a failed surgical procedure for the treatment of obesity, aside from reducing a volume of the pouch lumen, or reducing a diameter of the stoma through the pouch anastomosis, or even ablating the interior of the pouch lumen tissue surface, a length of the Roux limb may also be altered endoluminally. Altering the length of the Roux limb may create an additional malabsorptive portion of intestinal tissue and further reduce the ability of the patient body to absorb food passing therethrough. A rigidizable endoscopic body having a rounded atraumatic distal end may be advanced per-orally, through the patient's esophagus and pouch lumen, through the patient's pouch anastomosis and into the length of the intestinal tract.

The steerable distal portion of the endoscopic body may be articulated to curve into a retroflexed configuration relative to its proximal length while pulling a distal portion of the intestinal tract along with the endoscopic body into contact against or in proximity to the outer surface of the pouch. With the atraumatic distal end desirably positioned and the endoscopic body optionally rigidized, an endoscopic piercing or ablative instrument, e.g., an energizable needle knife, may be advanced through the distal portion of intestinal tissue and through the portion of pouch tissue to create an opening therebetween.

Once an opening through both tissue portions has been achieved, one or more tissue anchors may be deployed around the circumference of the openings using, e.g., tissue manipulation assembly, to secure the intestinal tissue to the pouch to create a side-to-side anastomotic connection. The anastomotic connection may be further dilated, if desired. Once the anastomotic connection has been formed, the endoscopic body may be transitioned into its flexible state (if initially rigidized) and withdrawn from the patient body. Optionally, the original pouch anastomosis may be closed using tissue anchors, if so desired, to ensure that food received within the pouch is shunted through the newly created anastomosis and bypasses the length of intestinal tissue. As a further option, the shunted portion of intestinal tissue may be endoluminally (or laparoscopically) excised and removed entirely from the patient body.

BRIEF DESCRIPTION OF THE DRAWINGS

FIG. IA shows the resulting anatomy of the stomach and intestinal tract from a Roux-en-Y gastric bypass procedure.

DETAILED DESCRIPTION OF THE INVENTION

To correct failed obesity procedures in a minimally invasive manner, a tissue manipulation and/or securement instrument may be introduced per-orally through the patient's esophagus and into the created pouch to perform a number of procedures. The pouch may have been previously formed by any number of procedures, e.g., RYGB, VBG, etc., for the treatment of obesity. Alternatively, the instrument may be introduced transgastrically, percutaneously, etc., into the patient's body and into or around the pouch. Once the instrument is positioned within or adjacent to the pouch, tissue within or from the pouch may be temporarily engaged or grasped and the engaged tissue may be manipulated by a surgeon or practitioner from outside the patient's body. Examples of creating and forming tissue plications may be seen in further detail in U.S. patent application Ser. No. 10/955,245 filed Sep. 29, 2004 as well as in U.S. patent application Ser. No. 10/735,030 filed Dec. 12, 2003, each of which is incorporated herein by reference in its entirety.

In engaging, manipulating, and/or securing the tissue, various methods and devices may be implemented. For instance, tissue securement devices may be delivered and positioned via an endoscopic apparatus for contacting a tissue wall of the pouch lumen, creating one or more tissue folds, and deploying one or more tissue anchors through the tissue fold(s). The tissue anchor(s) may be disposed through the muscularis and/or serosa layers of the pouch lumen. When manipulating and securing tissue within a patient's body, a separate elongate shaft having a helical tissue engager on or near the distal end of the shaft may be utilized in conjunction with a tissue manipulation assembly. Such an instrument may be generally utilized in endoluminal procedures where the tools are delivered through an endoscopic device.

Figure 1A:
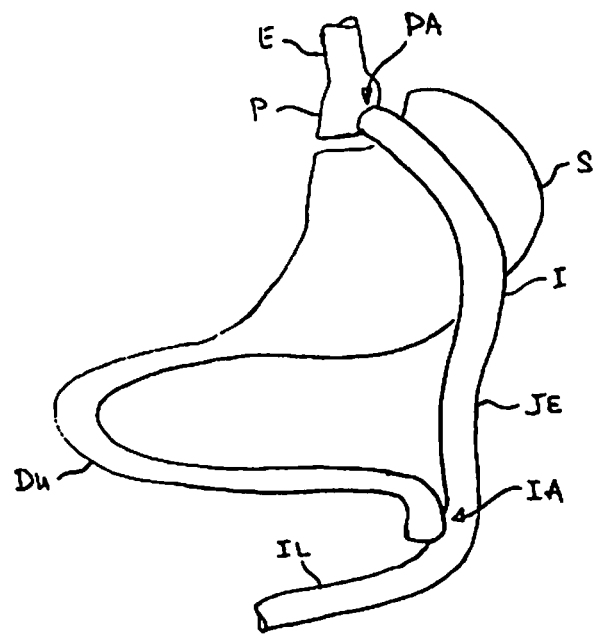
FIG. 1B shows the resulting anatomy of the stomach from a vertical banded gastroplasty procedure.
Figure 1B:
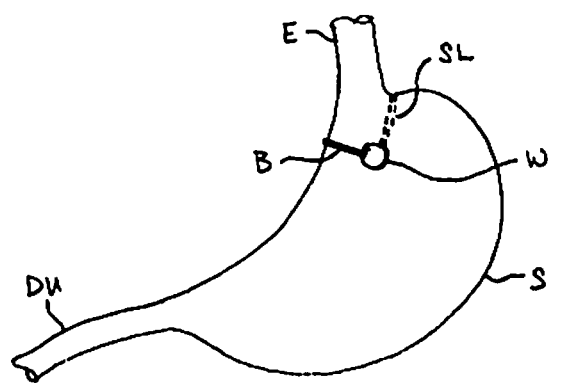
Figure 2:
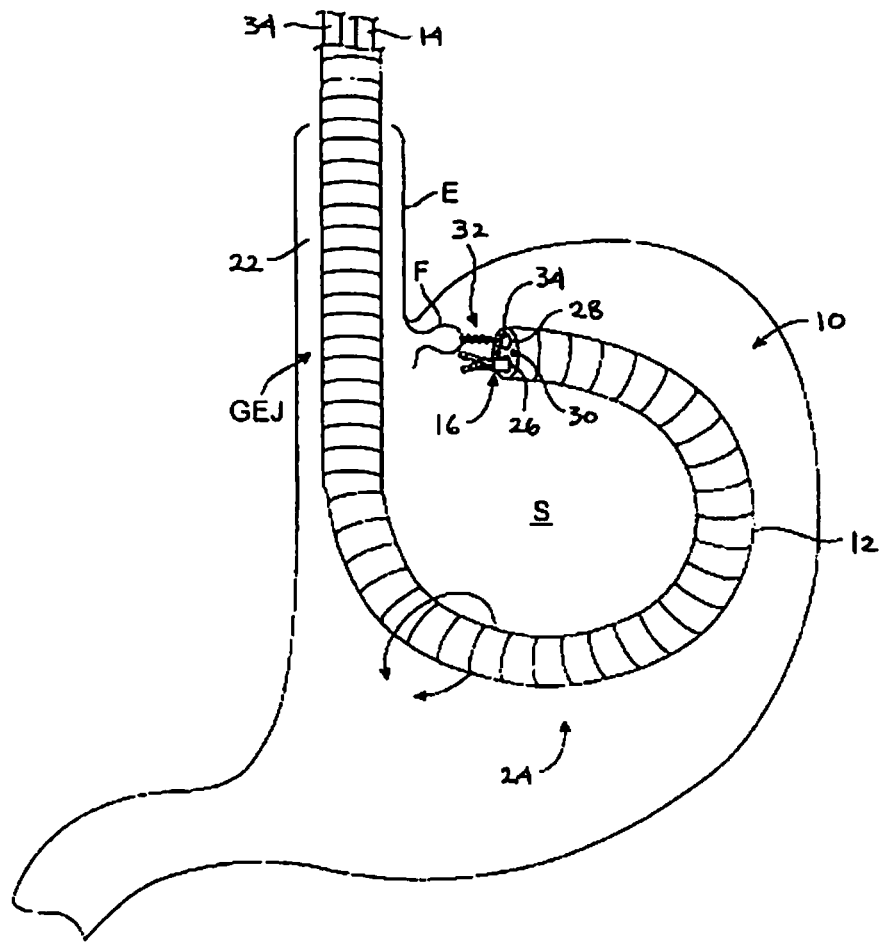
FIG. 2 illustrates one example in which a rigidizable endoscopic assembly may be advanced into a patient's stomach per-orally and through the esophagus with a tissue manipulation assembly advanced through a first lumen and a helical tissue engagement instrument advanced through a second lumen.

As illustrated in FIG. 2, one such example is shown in which a shape-lockable or rigidizable endoscopic assembly 10 may be advanced into a patient's stomach S per-orally and through the esophagus E. Such an endoscopic assembly 10 may generally comprise an endoscopic device which may have a distal portion which may be articulated and steered to position its distal end anywhere within the stomach S. Once desirably configured, assembly 10 may then be locked or rigidized to maintain its shape or configuration to allow for procedures to be performed on the tissue utilizing any number of tools delivered through the assembly 10. Shape-lockable or rigidizable assembly 10 and its variations are described in further detail in U.S. patent application Ser. No. 10/734,562 filed Dec. 12, 2003 and in U.S. patent application Ser. No. 10/346,709 filed Jan. 15, 2003, both of which are incorporated herein by reference in its entirety.

Shape-lockable assembly 10 may be generally comprised of shape-lockable endoscopic body 12 having an articulatable distal portion 24. The endoscopic body 12 may define at least first and second lumens 26, 28, respectively, through the endoscopic body 12 through which one or more tools may be deployed into the stomach S. Additional lumens may be provided through shape-lockable endoscopic body 12, such as a visualization lumen 30, through which an endoscope may be positioned to provide visualization of the region of tissue. Alternatively, an imager such as a CCD imager or optical fibers may be provided in lumen 30 to provide visualization. An optional thin wall sheath may be disposed through the patient's mouth, esophagus E, and possibly past the gastroesophageal junction GEJ into the stomach S. Shape-lockable body 12, having a covering 22 thereon, may be advanced through esophagus E and into stomach S while disposed in a flexible state.

Distal steerable portion 24 of endoscopic body 12 may be then articulated to an orientation, e.g., whereby distal portion 24 facilitates engagement of tissue near and/or inferior to the patient's gastroesophageal junction GEJ. Accordingly, distal steerable portion 24 may comprise a number of steering features, as described in further detail in U.S. patent application Ser. Nos. 10/734,562 and 10/346,709, incorporated above. With distal steerable portion 24 disposed in a desired configuration or orientation, endoscopic body 12 may be reversibly shape-locked to a rigid state such that the endoscopic body 12 maintains its position within the stomach S. Various methods and apparatus for rigidizing endoscopic body 12 along its length are also described in further detail in U.S. patent application Ser. Nos. 10/734,562 and 10/346,709, incorporated above.

FIG. 2 further shows tissue manipulation assembly 16 having been advanced through first lumen 26 and a helical tissue engagement member 32 positioned upon flexible shaft 34 advanced through second lumen 28. As the tissue wall of a body lumen, such as the stomach, typically comprises an inner mucosal layer, connective tissue, the muscularis layer and the serosa layer. To obtain a durable purchase, e.g., in performing a stomach reduction procedure, helical tissue engagement member 32 may be advanced into contact with the tissue and preferably engages the tissue F such that when the tissue engagement member 32 is pulled proximally to draw the engaged tissue F between the jaw members 18, 20 of tissue manipulation assembly 16, at least the muscularis tissue layer and the serosa layer is drawn into tissue manipulation assembly 16. As tissue manipulation assembly 16 may be utilized to grasp and secure the engaged tissue, any number of tools may be utilized with tissue manipulation assembly 16, e.g., through shape-lockable endoscopic body 12, to engage and manipulate the tissue of interest relative to tissue manipulation assembly 16.

An illustrative example of a tissue manipulation instrument which may be utilized for endoluminally accessing tissue is described in further detail in U.S. patent application Ser. No. 11/070,863 filed Mar. 1, 2005 (US Pat. Pub. 2005/0251166 A1), which is incorporated herein by reference in its entirety. Such an instrument assembly generally comprises a flexible catheter or tubular body 14 which may be configured to be sufficiently flexible for advancement into a body lumen, e.g., transorally, percutaneously, laparoscopically, etc. Tubular body 14 may be configured to be torqueable through various methods, e.g., utilizing a braided tubular construction, such that when a proximally-located handle is manipulated and/or rotated by a practitioner from outside the patient's body, the longitudinal and/or torquing force is transmitted along body 14 such that the distal end of body 14 is advanced, withdrawn, or rotated in a corresponding manner.

Figure 3A:
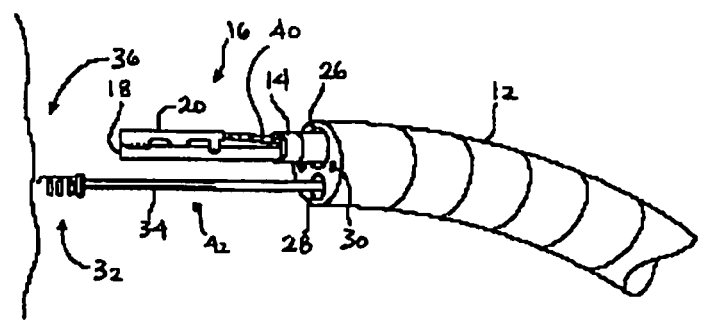
FIGS. 3A to 3C illustrate an example for performing an endoluminal tissue manipulation and securement procedure utilizing a tissue manipulation assembly in combination with a helical tissue engagement instrument within, e.g., a patient's altered stomach in a revision procedure.
Figure 3B:
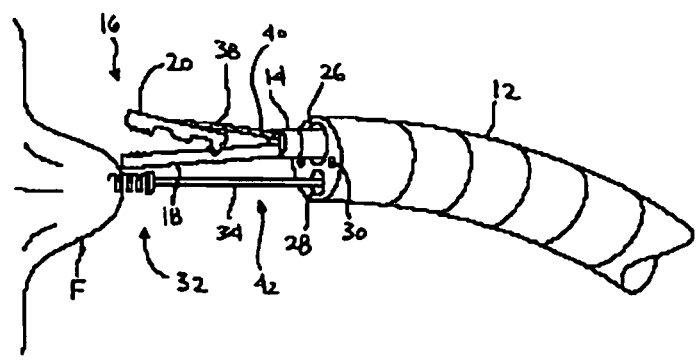
Figure 3C:
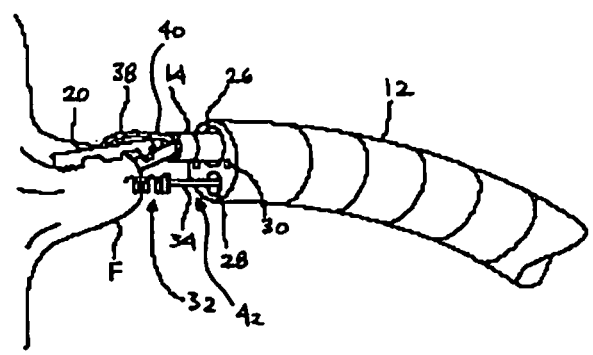

As shown in FIGS. 3A to 3C, tissue manipulation assembly 16 is located at the distal end of tubular body 14 and is generally used to contact and form tissue folds, as mentioned above. The tissue manipulation assembly 16 may be connected to the distal end of tubular body 14 via a pivotable coupling. Lower jaw member 18 extends distally from the pivotable coupling and upper jaw member 20, in this example, may be pivotably coupled to lower jaw member 18 via a jaw pivot. The location of the jaw pivot may be positioned at various locations along lower jaw 18 depending upon a number of factors, e.g., the desired size of the "bite" or opening for accepting tissue between the jaw members, the amount of closing force between the jaw members, etc. One or both jaw members 18, 20 may also have a number of protrusions, projections, grasping teeth, textured surfaces, etc., on the surface or surfaces of the jaw members 18, 20 facing one another to facilitate the adherence of tissue between the jaw members 18, 20.

Launch tube 40 may extend from the handle, through tubular body 14, and distally from the end of tubular body 14 where a distal end of launch tube 40 is pivotally connected to upper jaw member 20 at a launch tube pivot. A distal portion of launch tube 40 may be pivoted into position within a channel or groove defined in upper jaw member 20, to facilitate a low-profile configuration of tissue manipulation assembly 16. When articulated, either via launch tube 40 or other mechanism, as described further below, jaw members 18, 20 may be urged into an open configuration to receive tissue in the jaw opening between the jaw members 18, 20.

Launch tube 40 may be advanced from its proximal end at the handle such that the portion of launch tube 38, which extends distally from body 14, is forced to rotate at a hinge or pivot and reconfigure itself such that the exposed portion forms a curved or arcuate shape that positions the launch tube opening perpendicularly relative to upper jaw member 20. Launch tube 40, or at least the exposed portion of launch tube 38, may be fabricated from a highly flexible material or it may be fabricated, e.g., from Nitinol tubing material which is adapted to flex, e.g., via circumferential slots, to permit bending.

FIGS. 3A to 3C further illustrate one method for articulating a tissue manipulation assembly into an opened and closed configuration. As shown in FIG. 3A, the assembly may be delivered into a patient while in a low-profile configuration 40, e.g., trans-orally, trans-anally, percutaneously, through an endoscope, an endoscopic device, directly, etc., and desirably positioned relative to a tissue region of interest 36. The endoscopic body 12 may be rigidized to maintain its configuration within the patient body. Alternatively, it may be left in a flexible state during the procedure.

The tissue region of interest 36 as well as the procedure may be visualized through visualization lumen 30 or a separate imager. In either case, tissue manipulation assembly 16 and helical tissue engagement member 32 may be advanced distally out from endoscopic body 12 through their respective lumens 26, 28. Tissue engagement member 32 may be advanced into contact against the tissue surface, as shown in FIG. 3A, and then rotated via its proximal handle until the tissue is engaged. The engaged tissue F may be pulled proximally relative to endoscopic body 12 and tissue manipulation assembly 16 may be actuated via its proximally located handle into an open expanded jaw configuration for receiving the engaged tissue F, as shown in FIG. 3B.

Once desirably positioned, launch tube 40 may be urged proximally via its proximal end at the handle. Because of the jaw assembly pivot and the relative positioning of the upper jaw 20 along lower jaw member 18 and the launch tube pivot along upper jaw member 20, the proximal movement of launch tube 40 may effectively articulate upper jaw 20 into an expanded jaw configuration, as shown in FIG. 3B. Proximally urging launch tube 40 may also urge lower jaw member 18 to pivot and form an angle relative to a longitudinal axis of tubular body 14. The opening of upper jaw 20 relative to lower jaw 18 creates a jaw opening for grasping, receiving, and/or manipulating tissue. Moreover, the tissue manipulation assembly may also include a stop located adjacent to the jaw assembly pivot or within the pivot itself.

Once launch tube 40 has been urged proximally, it may be locked into place thus locking the jaw configuration as well. Moreover, having the launch tube 40 articulate the jaw members 18, 20 in this variation eliminates the need for a separate jaw articulation and/or locking mechanism. Once the tissue has been pulled or manipulated between jaw members 18, 20, launch tube 40 may be pushed distally to actuate the jaw members 18, 20 into a closed, grasping configuration, as shown in FIG. 3C, for engagement with the tissue. As launch tube 40 is urged distally through elongate body 12, lower jaw member 18 may be maintained at an angle relative to the tissue to further facilitate manipulation of the grasped tissue.

Although launch tube 40 may be fabricated from different materials having differing flexibilities, it may also be fabricated from a single material, as mentioned above, where the flexible portion 38 may be configured, e.g., by slotting, to allow for bending of the launch tube 40 in a plane to form a single curved or arcuate section while the proximal rigid section may extend at least partially into tubular body 14 to provide column strength to launch tube 40 while it is urged distally upon upper jaw member 20 and upon any tissue engaged thereby, as seen in the FIG. 3C.

Once the tissue has been engaged between jaw members 18, 20, a needle assembly may be urged through the handle and out through launch tube 40. The needle assembly may pass through lower jaw member 18 via a needle assembly opening defined in lower jaw member 18 to pierce through the grasped tissue. Once the needle assembly has been passed through the engaged tissue, one or more tissue anchors may be deployed for securing the tissue, as described in further detail in U.S. patent application Ser. No. 10/955,245, which has been incorporated by reference above.

Helical tissue engagement member 32 may be retracted from the tissue F or it may be left within the tissue while the tissue manipulation assembly engages and secures the tissue F. The helical tissue engagement member 32 is shown as a tissue piercing helix or corkscrew structure upon flexible shaft 34. Tissue engagement member 32 may be rotated about its longitudinal axis to engage the tissue of interest by rotating its handle located on the proximal end of flexible shaft 34.

A distal portion of shaft 34 proximal to engagement member 32 (or the entire length or a majority of the length of shaft 34 in other variation's) may include a marked section 42, as shown in FIGS. 3A to 3C. Helical tissue engagement member 32 and flexible shaft 34 are rotated about its longitudinal axis to advance engagement member 32 into the tissue region of interest 36. Accordingly, marked section 42 may comprise any number of markings, designs, patterns, projections, textures, etc., which acts to provide a visual indication to the user as to the translational movement, rotation, direction of rotation, etc., of engagement member 32 and shaft 34 relative to tissue region 36 when viewed from outside the patient body laparoscopically or endoluminally, for instance, through visual lumen 30.

Figure 4A:
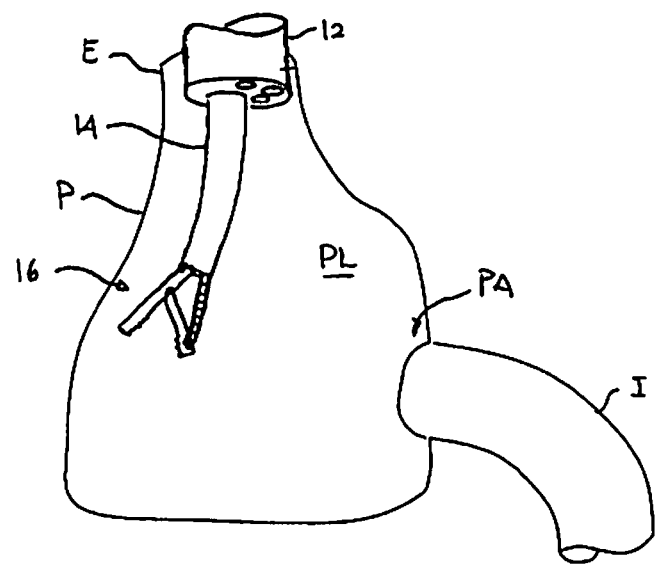
FIGS. 4A and 4B show detail views, respectively, of a failed pouch and a repaired pouch having a plurality of tissue folds secured throughout an interior of the pouch to reduce its size.

Utilizing the instruments described above, various endoluminal procedures may be performed to correct failures in obesity-related procedures. For example, FIG. 4A shows a detail view of a pouch P which may have failed, e.g., through a stretched and enlarged pouch lumen PL. The remaining anatomy, such as the remainder of the stomach S, has been omitted only for clarity. The flexible body 14 and tissue manipulation assembly 16, described above, may be advanced per-orally, through the esophagus E, and into the enlarged pouch lumen PL. The rigidizable endoscopic body 12 may be used to pass the flexible body 14 therethrough and into pouch P, as shown in the figure. In an alternative method (and for methods described below), the endoscopic body 12 may be omitted entirely and flexible body 14 and tissue manipulation assembly 16 may be passed directly into the pouch P.

Figure 4B:
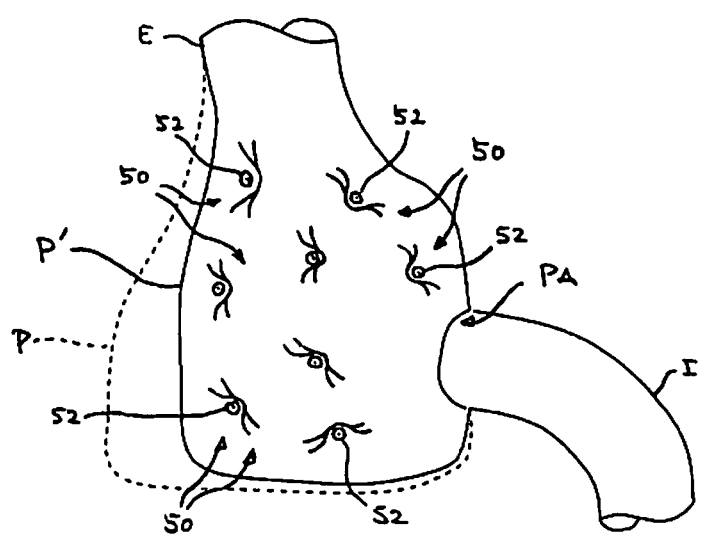

Once within the pouch lumen PL, the tissue manipulation assembly 16 may be used to create within the pouch P approximated folds of tissue 50 which are secured via expandable tissue anchors 52 expelled from the tissue manipulation assembly 16, as described above. Any number of tissue folds 50, i.e., one or more, may be created in a uniform pattern or randomly throughout the pouch lumen PL, as shown in FIG. 4B, such that the enlarged pouch P is reduced in size to a pouch P' having a smaller volume.

Figure 5A:
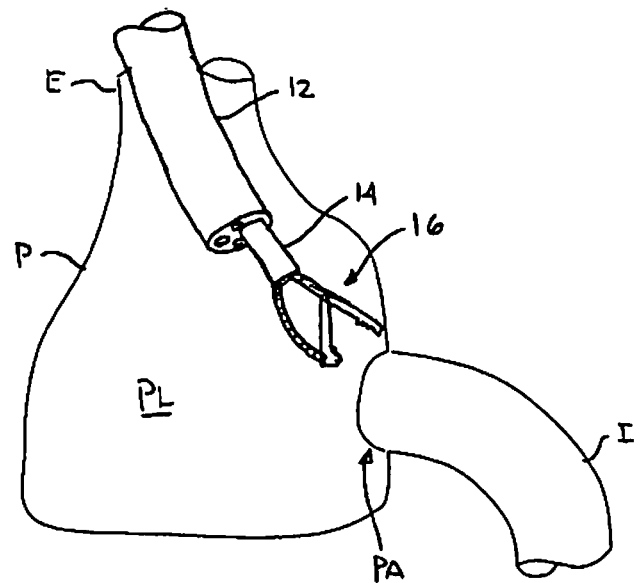
FIGS. 5A and 5B show detail views, respectively, of a failed pouch and a pouch with its anastomotic opening reduced in diameter to further restrict the passage of food therethrough.
Figure 5B:
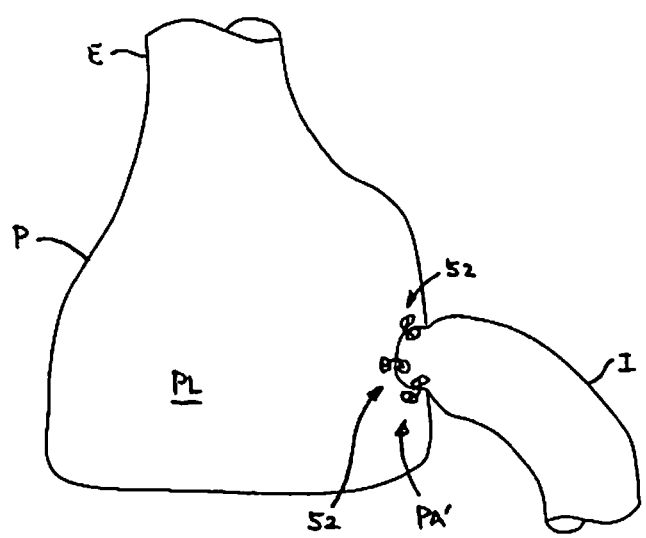

Another method may involve endoluminally reducing a diameter or size of the stoma created between the pouch lumen PL and the intestinal tract I through the pouch anastomosis PA. As shown in FIG. 5A, flexible body 14 and tissue manipulation assembly 16 may be advanced through the patient's esophagus E and into the pouch lumen PL either alone or optionally through endoscopic body 12, as illustrated. Once within the pouch P, tissue manipulation assembly 16 may be directed to the tissue circumferentially around the anastomotic connection PA, where the tissue from pouch P and a portion of the tissue from the intestinal tract I around the pouch anastomosis PA may be approximated by tissue manipulation assembly 16 and secured by one or more pairs of tissue anchors 52, as shown in FIG. 5B. One pair or several pairs of tissue anchors 52 may be deployed into the tissue randomly or in a uniformly spaced configuration around the pouch anastomosis PA provided that the enlarged opening through pouch anastomosis PA is reduced in size to a smaller pouch anastomosis PA' opening which is more effective in restricting the passage of food received within pouch lumen PL.

Figure 5C:
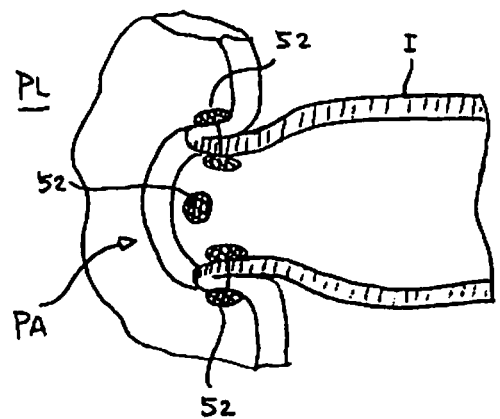
FIGS. 5C and 5D show partial cross-sectional views of reduced stomas where a portion of the anastomosed intestinal tissue is approximated with respect to the pouch and where a portion of the pouch tissue is plicated leaving the anastomosed intestinal tissue untouched, respectively.
Figure 5D:
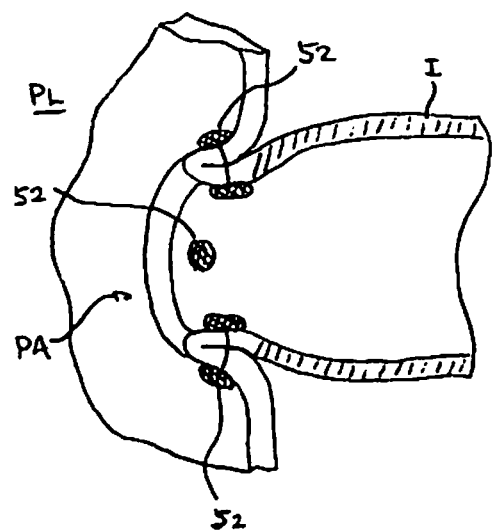

There are a number of methods for reducing the stoma size by varying the configuration of the tissue anchors deployed around the stoma. For instance, the example illustrated in FIG. 5C shows a partial cross-sectional side view of a reduced stoma through a pouch anastomosis PA where a portion of the anastomosed intestinal tissue I and a portion of the pouch tissue may be approximated around the stoma via one or more anchor pairs 52 deployed and secured against the tissue. In another variation, rather than approximating the intestinal tissue I, the portion of pouch tissue adjacent to or in proximity to the pouch anastomosis PA may be plicated such that the intestinal tissue I remains untouched, as shown in FIG. 5D.

Figure 5E:
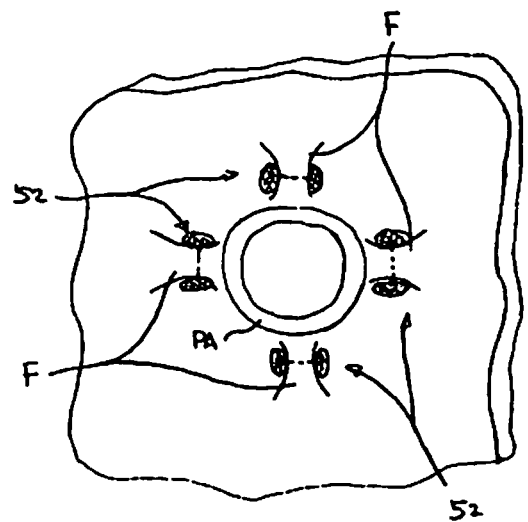
FIGS. 5E and 5F show end views from within the pouch of the stoma and pouch anastomosis where the pouch tissue adjacent to the stoma may be approximated in a radial configuration and/or a circumferential or annular configuration, respectively.
Figure 5F:
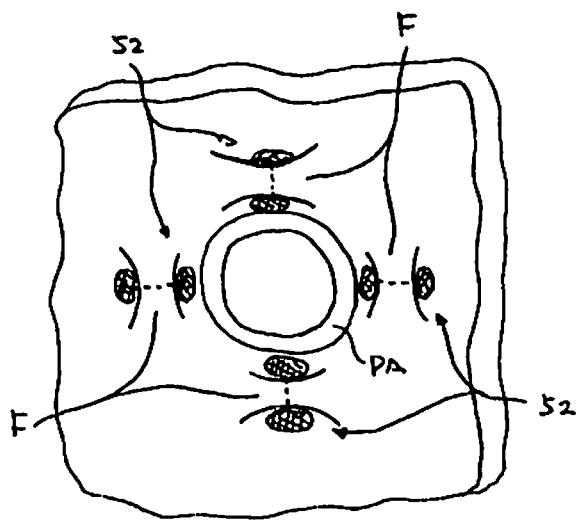

In yet other examples, the tissue from the pouch adjacent to the pouch anastomosis PA may be approximated and secured to reduce the stoma size. As shown in the end view from within the pouch of the stoma and pouch anastomosis PA in FIG. 5E, one or more anchor pairs 52 may be deployed into the pouch tissue to form one or more folds of tissue F which are formed radially with respect to the pouch anastomosis PA. In another example shown in FIG. 5F, one or more tissue folds F may be formed and secured such that the tissue folds F are circumferentially or more annularly aligned with respect to the stoma and pouch anastomosis PA.

Figure 6A:
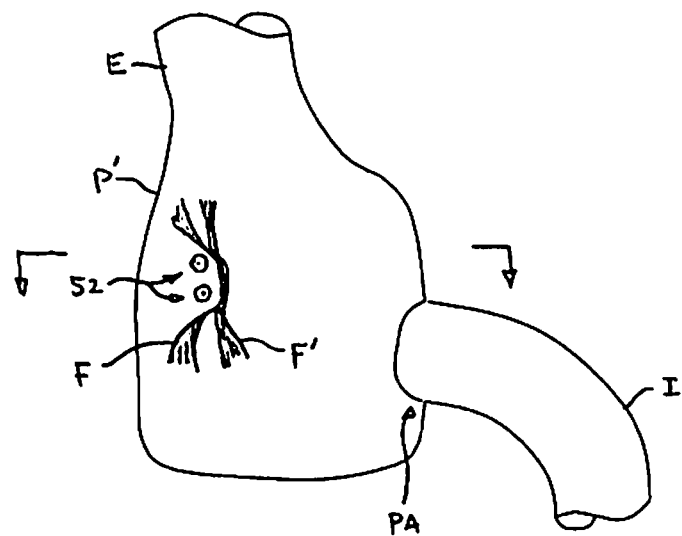
FIGS. 6A and 6B show detail views, respectively, of a pouch having a portion of its interior approximated and a cross-sectional top view of the same.
Figure 6B:
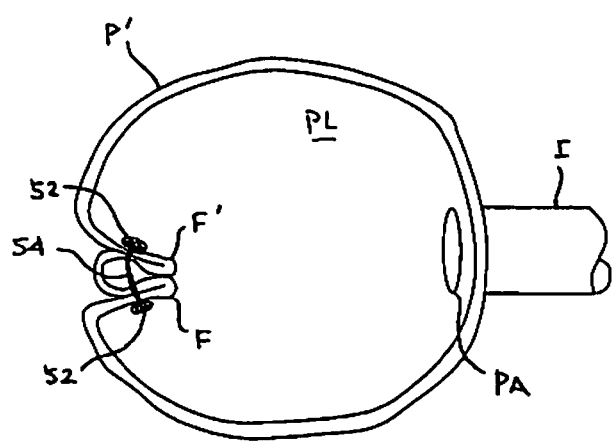

FIGS. 6A and 6B show detail perspective and cross-sectional top views of a reduced pouch lumen PL by approximating multiple folds of tissue within the pouch P. The tissue manipulation assembly 16 may be advanced into the pouch P and at least a first fold of tissue F may be approximated to at least a second fold of tissue F' and secured via one or more pairs of tissue anchors 52. FIG. 6B shows a cross-sectional view of the reduced pouch P' where the first fold of tissue F and the second fold of tissue F' are secured to one another by the tissue anchors 52 one either side of the respective tissue folds F, F' via a length of suture 54 passing through and securing each fold F, F'. Although a single tissue apposition is shown in this example, multiple folds of tissue may be approximated towards one another around the pouch lumen PL until the desired reduction in the pouch lumen volume has been achieved.

Figure 7A:
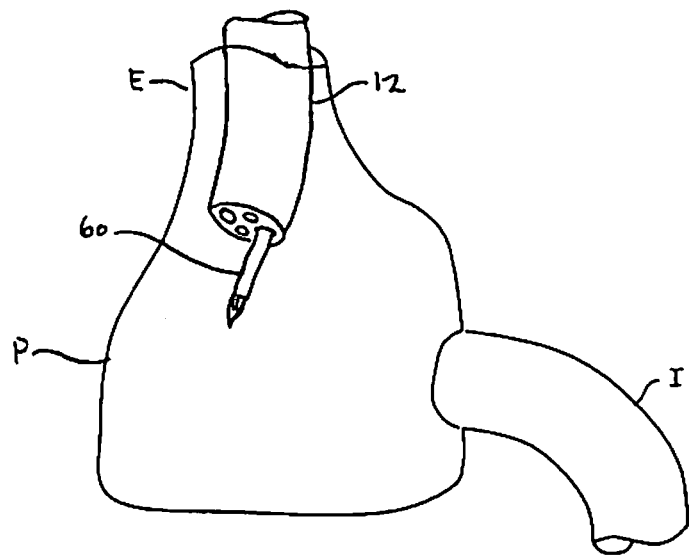
FIGS. 7A and 7B show detail views, respectively, of a failed pouch and a pouch having at least a portion of its interior surface injured and/or ablated to reduce the pouch size.
Figure 7B:
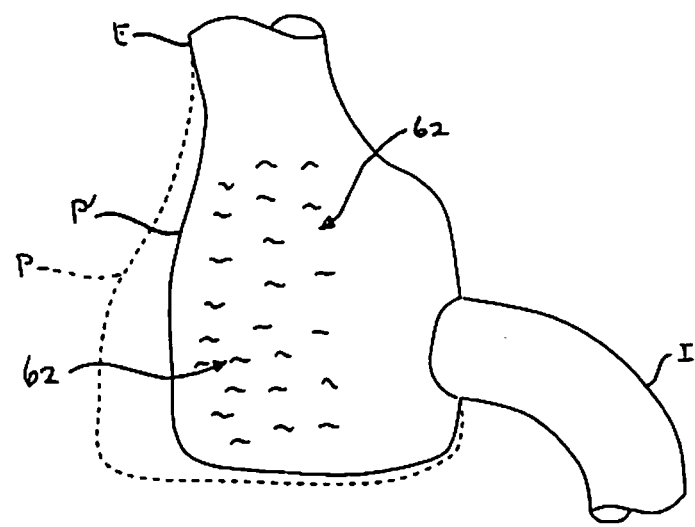

FIG. 7A shows an example of a method where an endoluminal tissue ablation instrument 60, e.g., plasma torch, laser, radio-frequency probe, etc., may be advanced through the endoscopic body 12 and into the pouch P. This ablation instrument 60 may be activated to ablate one or more regions of tissue 62 within pouch P, particularly the mucosal tissue, such that the shrinkage of the ablated tissue within pouch lumen PL shrinks the size of the pouch P to a reduced pouch P', as shown in FIG. 7B. Examples of other tools and instruments for injuring regions of tissue and mucosa are shown and described in further detail in U.S. patent application Ser. No. 10/898,683 filed Jul. 23, 2004, which is incorporated herein by reference in its entirety.

Figure 8A:
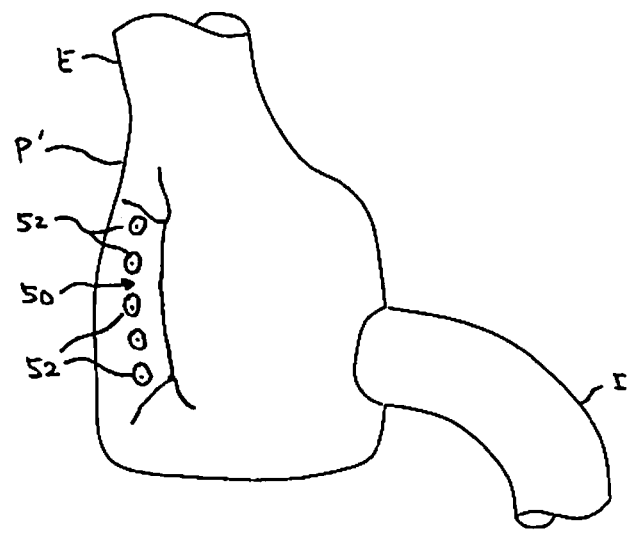
FIGS. 8A and 8B show detail views, respectively, of a pouch having a portion of its interior approximated and removed to promote healing of the plicated tissue.
Figure 8B:
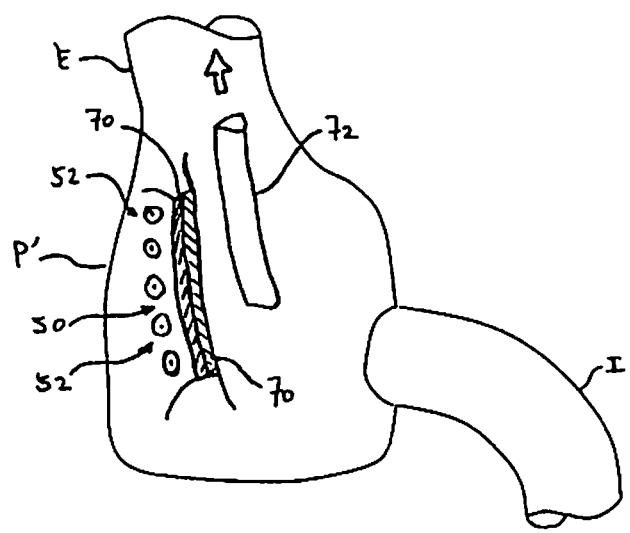

FIG. 8A shows an example of another method where one or more ridges of tissue may be plicated to form at least one tissue fold which is secured by one or more tissue anchors 52 to reduce the side of a pouch P'. To enhance the healing of the tissue fold, a portion of the tissue 72 may be optionally resected or otherwise injured to leave a region of injured or sclerosed tissue 70 along the tissue fold, as shown in FIG. 8B. Injuring or removing tissue 72 is optional and may be performed on any of the tissue folds created within pouch lumen PL if additional healing of the tissue is desired. Examples of methods and instruments which may be utilized to resect and/or remove tissue from within a lumen, such as pouch lumen PL, may be seen in U.S. patent application Ser. No. 11/069,890 filed Feb. 28, 2005, which is incorporated herein by reference in its entirety.

To facilitate the grasping and manipulation of the tissue within the pouch P, various methods and instruments may be utilized. In one example, a tissue engagement member, such as member 32, may be positioned through elongate body 12 and utilized with tissue manipulation assembly 16, as described above. In another example, the tissue manipulation assembly 16 may be positioned within pouch lumen PL with lower and upper jaw members 18, 20 positioned in an open configuration for receiving tissue therebetween. The air, along with any other fluids, contained within pouch lumen PL may be evacuated out, e.g., through one of the lumens defined through elongate body 12 or through a catheter advanced through body 12. The evacuation of air and fluids from pouch lumen PL may collapse the pouch tissue onto the flexible body 14 and between the jaw members 18, 20.

Figure 9A:
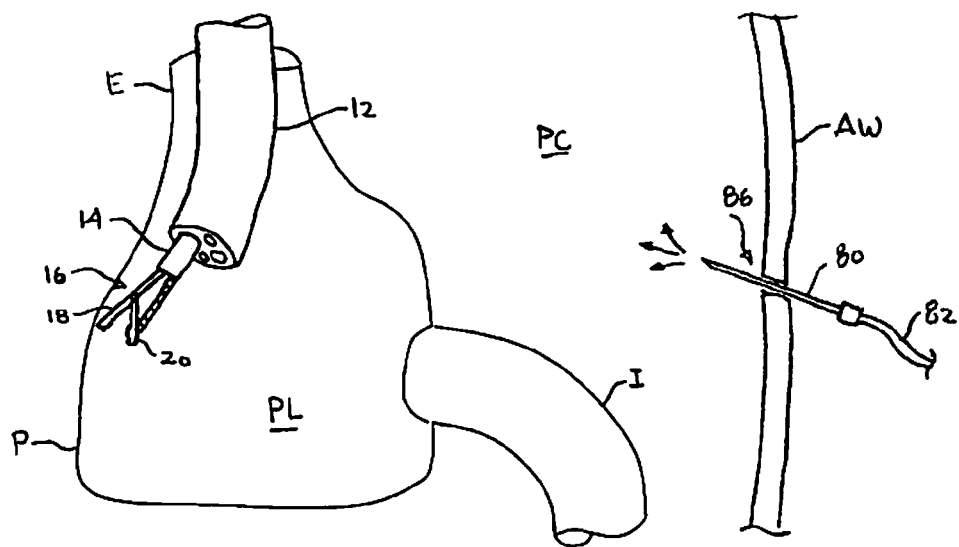
FIGS. 9A and 9B illustrate detail views of one method for facilitating the grasping and engagement of the tissue within the interior of the tissue pouch by insufflating a patient's peritoneal cavity to collapse the pouch tissue upon the tissue manipulation assembly.
Figure 9B:
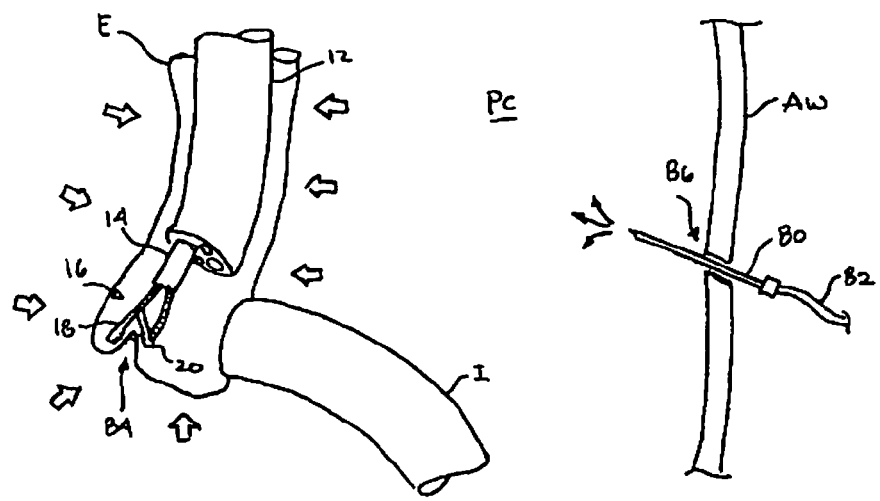

In yet another example shown in FIG. 9A, a hollow instrument, such as Verres needle 80, may be advanced percutaneously and positioned through an opening 86 defined through the abdominal wall AW of a patient. Verres needle 80 may be fluidly connected via tubing 82 to a pump (not shown) such that a gas (e.g., air, carbon dioxide, nitrogen, etc.) may be pumped into the peritoneal cavity PC of the patient body. As more gas is introduced into the peritoneal cavity PC, the tissue of pouch P may become collapsed due to a pressure differential onto and over the tissue manipulation assembly 16, particularly between jaw members 18, 20 which may be positioned within pouch lumen PL prior to insufflating the peritoneal cavity PC with a gas, as shown in FIG. 9B. The collapsed pouch tissue 84 positioned between jaw members 18, 20 may then be easily grasped and secured by deploying one or more tissue anchors through the collapsed pouch tissue 84. The gas within the peritoneal cavity PC may be evacuated to allow for the tissue manipulation assembly 16 to be repositioned within the pouch and the process of re-filling the peritoneal cavity PC with gas may be repeated. This method of insufflating the peritoneal cavity PC may be utilized either alone or in conjunction with insufflating and exsufflating the gas and fluids within the pouch lumen PL itself through the elongate body 12, as described above.

Figure 10A:
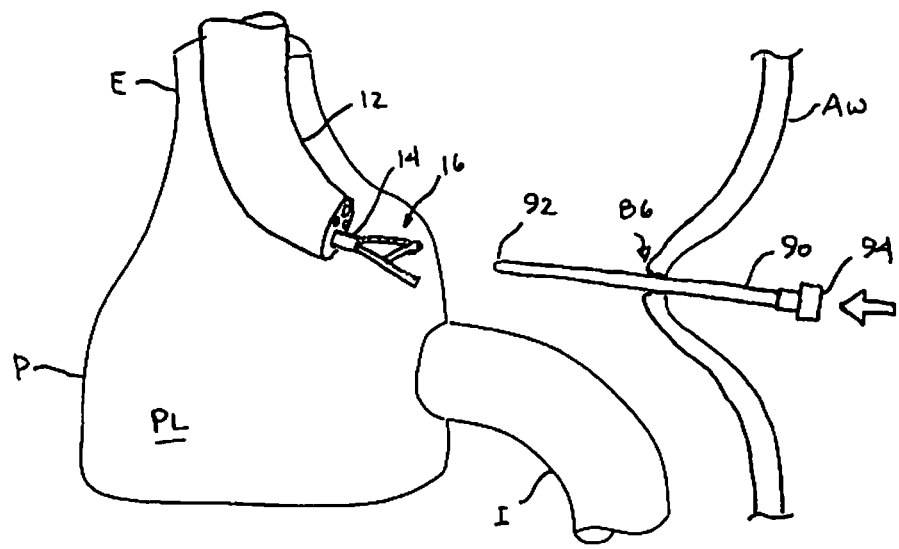
FIGS. 10A and 10B illustrate another method for facilitating tissue grasping and engagement within the pouch lumen by advancing an elongate laparoscopic instrument through a percutaneous opening and into contact with an outer surface of the pouch.
Figure 10B:
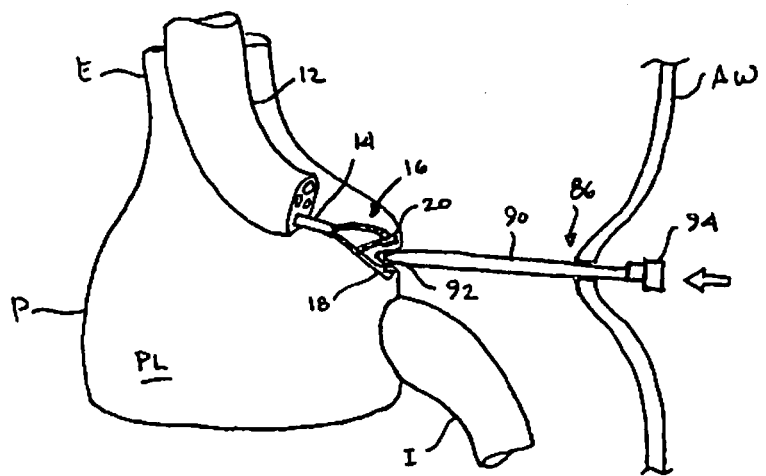

In yet another method for facilitating engagement of the interior tissue, an elongate laparoscopic instrument 90 having a blunted atraumatic tip 92 may be advanced through a percutaneous opening 86 and into contact with an outer surface of the pouch P. As shown in FIG. 10A, laparoscopic instrument 90 may be advanced distally through the peritoneal cavity via handle 94 with tissue manipulation assembly 16 positioned within the pouch lumen PL. Once the atraumatic tip 92 contacts the outer surface of the pouch P, laparoscopic instrument 90 may be pushed against the outer surface of pouch P such that a fold of tissue is formed within the pouch lumen PL in the proximity of the tissue manipulation assembly 16, as shown in FIG. 10B. To further facilitate the formation of the tissue fold, the interior of the pouch lumen PL may be insufflated with a gas to present a taut surface of the pouch tissue around the tissue fold.

With the tissue fold formed within the pouch lumen PL around the atraumatic tip 92, the jaw members 18, 20 of tissue manipulation assembly 16 may be positioned on either side of the tissue fold to grasp and secure the tissue, as further shown in FIG. 10B. Once the tissue fold has been secured, laparoscopic instrument 90 may be repositioned at another location on the outer surface of the pouch P. This process may be repeated as many times as necessary until a desired reduction in the pouch size has been attained. Moreover, the tissue folds may be formed in a uniform manner around the pouch lumen PL or in a random manner, as desired and as described above.

Figure 11A:
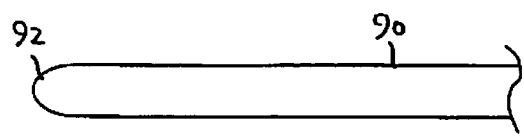
FIGS. 11A to 11C show examples of various laparoscopic instruments which may be passed through the patient body into contact with the pouch exterior.
Figure 11B:
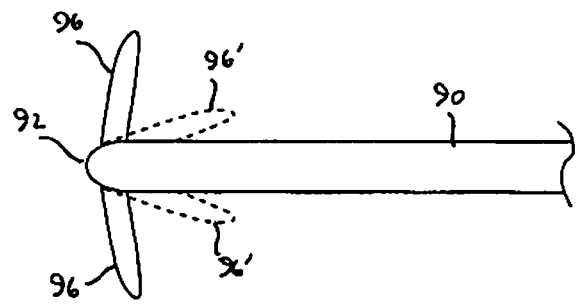
Figure 11C:
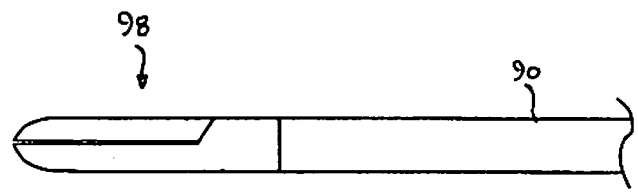

Various laparoscopic instruments may be utilized for forming the tissue bulges within the pouch lumen PL. An elongate shaft 90 having a simple blunted or rounded atraumatic tip 92, as described above and as shown in FIG. 11A, may be utilized. Alternatively, an elongate laparoscopic instrument having a variable geometry on its distal end may be utilized. Having such a variable geometry may be useful when advancing the instrument in the patient body in a low profile and expanded prior to contacting the pouch outer surface to form tissue folds having various geometries within the pouch. One example is shown in FIG. 11B where an elongate shaft 90 may have one or more retractable arms 96 which can pivot into a deployed configuration for contacting against the pouch outer surface and retracted 96' during delivery and withdrawal of the instrument 90 within the patient body. In another alternative, any laparoscopic instrument having a blunted distal shape may be utilized in forming the tissue folds. For example, FIG. 11C shows an elongate shaft 90 having a conventional laparoscopic grasper 98 attached thereto. The grasper 98 may be utilized in its closed configuration to press against the pouch outer surface, as described above.

In yet another alternative, rather than using a laparoscopic instrument, the finger or fingers of the surgeon or practitioner may simply be used to press against the outer surface of the patient body and against the pouch tissue surface to form the tissue folds within the pouch for securement by the tissue manipulation assembly 16. In any of the above described examples, the interior of the pouch lumen PL may be optionally insufflated by a gas during the tissue forming procedure.

In endoluminally revising a failed surgical procedure for the treatment of obesity, aside from reducing a volume of the pouch lumen, or reducing a diameter of the stoma through the pouch anastomosis PA, or even ablating the interior of the pouch lumen PL tissue surface, a length of the Roux limb may also be altered endoluminally. Altering the length of the Roux limb may create an additional malabsorptive portion of intestinal tissue and further reduce the ability of the patient body to absorb food passing therethrough.

Figure 12A:
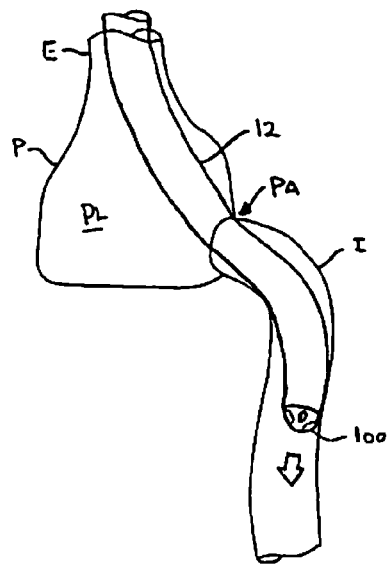
FIGS. 12A to 12C illustrate an example for altering a length of the Roux limb by advancing an optionally rigidizable elongate body through the pouch and intestinal tract and retroflexing a distal portion of the intestinal tissue for connection with the pouch.

As shown in FIG. 12A, a failed RYGB procedure with a pouch P and its anastomosed intestinal tract I is illustrated. A rigidizable endoscopic body 12 having a rounded atraumatic distal end 100 may be advanced per-orally, through the patient's esophagus E and pouch lumen PL, through the patient's pouch anastomosis PA and into the length of the intestinal tract I.

Figure 12B:
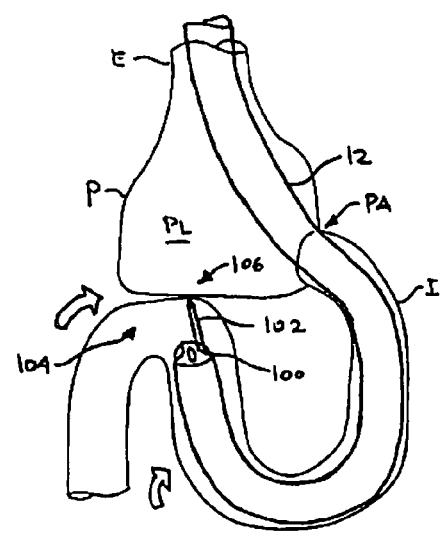

As described above, at least a portion of a length of endoscopic body 12 is transitionable between a flexible state and a rigid state and may have an articulatable or steerable distal portion 24. As the endoscopic body 12 in its flexible state is advanced a distance through the intestinal tract I, its steerable distal portion may be articulated to curve into a retroflexed configuration relative to its proximal length. As the endoscopic body 12 is retroflexed, a distal portion 104 of the intestinal tract I along the jejunum JE or ilium IL may be pulled along by the endoscopic body 12 into contact against or in proximity to the outer surface of the pouch P, as shown in FIG. 12B.

Figure 12C:
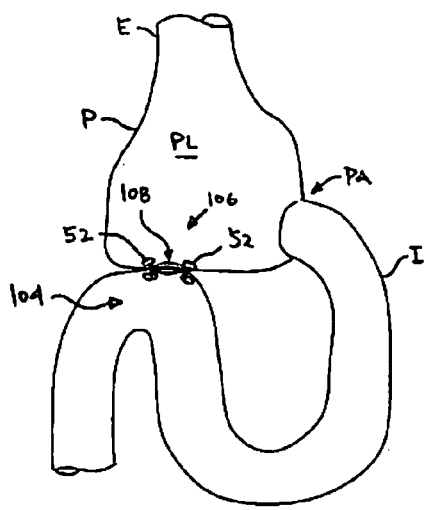

Once the endoscopic body 12 and distal portion 104 of the intestinal tract has been desirably positioned relative to the pouch P, endoscopic body 12 may be optionally transitioned into its rigid state to provide a stable platform for cutting or piercing through the distal portion 104 and pouch P for creating an anastomotic connection therebetween. With the atraumatic distal end 100 desirably positioned and endoscopic body 12 optionally rigidized, an endoscopic piercing or ablative instrument 102, e.g., an energizable needle knife, may be advanced through the distal portion 104 of intestinal tissue and through the portion of pouch tissue 106. Once an opening through both tissue portions has been achieved, one or more tissue anchors 52 may be deployed around the circumference of the openings using, e.g., tissue manipulation assembly 16, to secure the intestinal tissue I to the pouch P to create a side-to-side anastomotic connection 108, as shown in FIG. 12C. The anastomotic connection 108 may be further dilated, if desired, by utilizing additional instruments such as balloons, sphincterotomes, etc. Once the anastomotic connection 108 has been formed, the endoscopic body 12 may be transitioned into its flexible state (if initially rigidized) and withdrawn from the patient body.

Optionally, the original pouch anastomosis PA may be closed using tissue anchors 52, if so desired, to ensure that food received within the pouch P is shunted through the newly created anastomosis 108 and bypasses the length of intestinal tissue I.

Figure 12D:
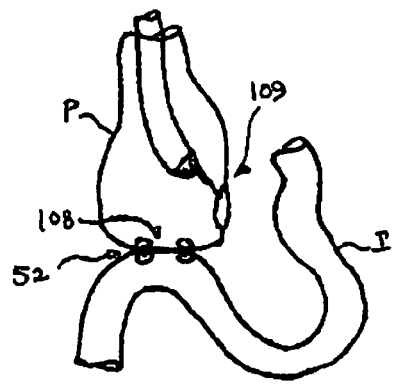
FIGS. 12D to 12G illustrate an optional procedure for endoluminally excising and removing a portion of the Roux limb proximally through the pouch and esophagus and from the patient's mouth.

Additionally and/or optionally, one or more portions of the intestinal tissue may be excised and removed entirely from the patient body by withdrawing the excised tissue proximally through a natural orifice of the patient body, for instance, from and/or through the pouch, esophagus, and out of the patient's mouth. One example is shown in FIGS. 12D to 12G where after the pouch P has been shunted through the newly created anastomosis 108, the rigidizable endoscopic body 12 may be directed towards the pouch anastomosis PA where a cutting or piercing instrument, such as instrument 102, may be used to cut away the anastomosed intestinal portion I from the pouch P to leave a pouch opening 109, as shown in FIG. 12D.

Figure 12E:
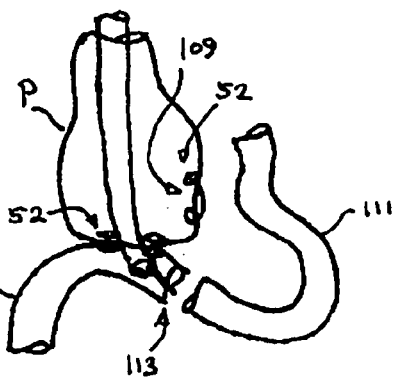
Figure 12F:
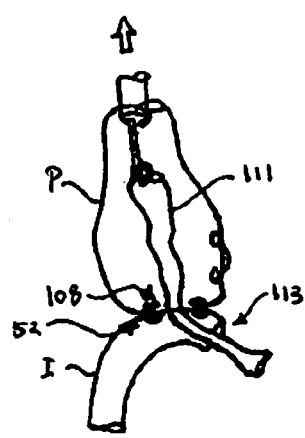
Figure 12G:
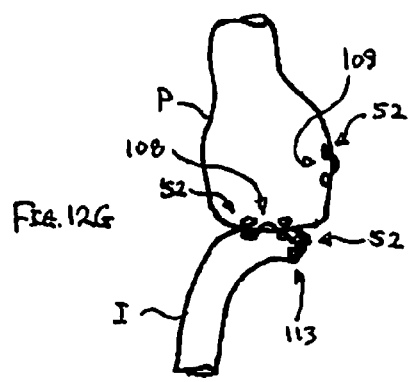

With the previously anastomosed intestinal tissue I cut from pouch P, the pouch opening 109 may be closed via one or more tissue anchors 52, as shown in FIG. 12E, using the tissue manipulation assembly 16. The endoscopic body 12 may be redirected through the anastomosis 108 where instrument 102 may be advanced at least partially into the intestinal tissue I to completely excise the portion of intestinal tissue 111. As shown in FIG. 12F, the excised intestinal tissue 111 may be grasped or otherwise secured via the tissue manipulation assembly 16 (or endoscopic graspers or other engaging instrument) and withdrawn proximally through the intestinal opening 113, anastomosis 108, pouch P, and through the patient esophagus and out of the patient's mouth. After the excised intestinal tissue 111 has been removed from the patient body, the endoscopic body 12 (or just the tissue manipulation assembly 16) may be advanced back into pouch P and through the anastomosis 108 to deploy one or more additional tissue anchors 52 to close the intestinal tissue opening 113, as shown in FIG. 12G. The instruments may then be withdrawn proximally and removed from the patient body entirely.

In yet another method for reducing a size of the pouch lumen PL, endoscopic body 12 may be advanced through a transgastric opening 110 created along the pouch wall. The transgastric opening 110 may be formed by utilizing endoluminal cutting and/or piercing instruments or by utilizing laparoscopic instruments passed through the patient's abdominal wall. In either case, the endoscopic body 12 may be passed through the transgastric opening 110 and into the peritoneal cavity of the patient body.

Figure 13A:
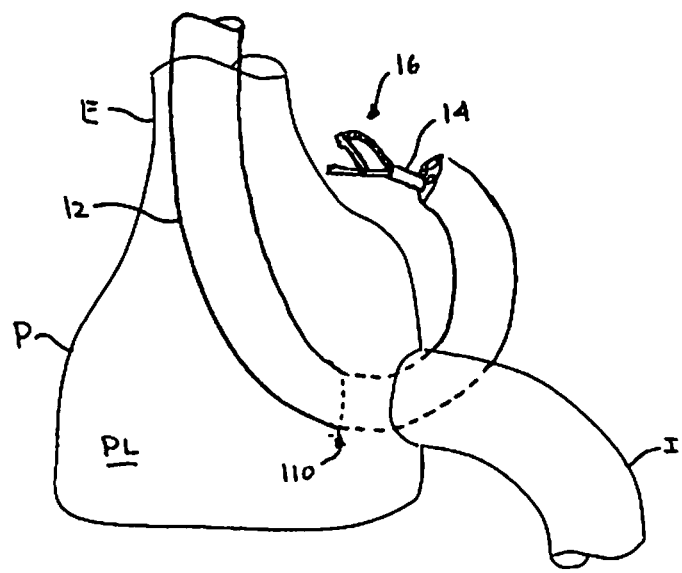
FIGS. 13A and 13B show another example for reducing a size of a pouch by creating at least one externally formed tissue ridge along the outer surface of the pouch.
Figure 13B:
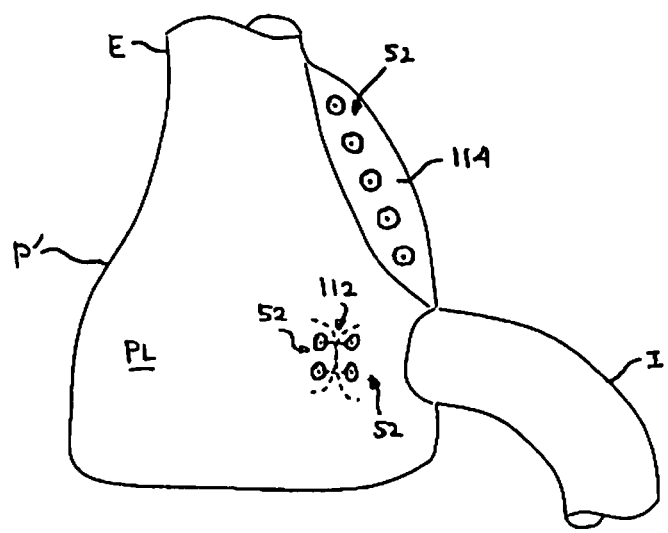

Once within the peritoneal cavity, the endoscopic body 12 may be steered and/or retroflexed to direct the tissue manipulation assembly 16 adjacent to the outer surface of the pouch P, as shown in FIG. 13A. From there, tissue manipulation assembly 16 may be utilized to create at least one (or more) externally formed tissue ridge 114 by deploying one or more tissue anchors 52 along the outer surface of the pouch P. As the tissue is plicated and secured, the interior of the pouch lumen PL may be reduced in size to form a smaller pouch P', as shown in FIG. 13B. Once the pouch P' has been desirably reduced in size, the endoscopic body 12 may be withdrawn proximally through the transgastric opening 110, which may then be closed by deploying one or more tissue anchors 52 to close the opening 112.

Examples for creating and/or closing transgastric openings as well as passing endoluminal instruments through the transgastric openings may be seen in further detail in U.S. patent application Ser. No. 11/238,279 filed Sep. 28, 2005 and U.S. Prov. Pat. App. Ser. No. 60/728,382 filed Oct. 18, 2005, each of which is incorporated herein by reference in its entirety.

Figure 14A:
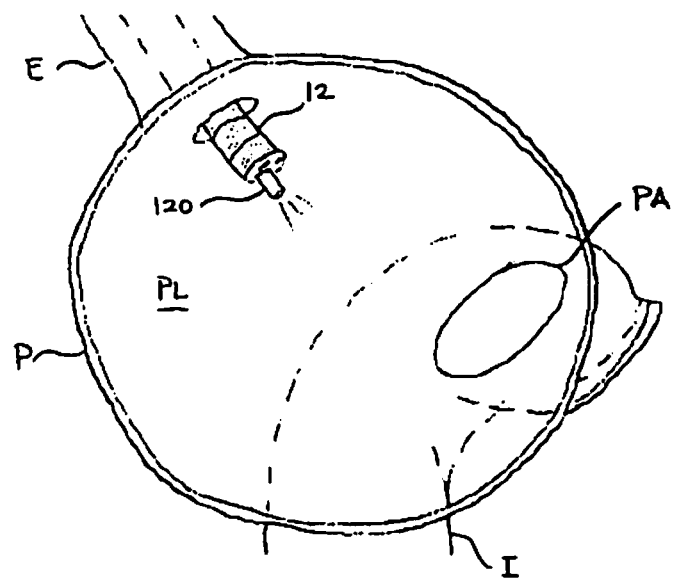
FIGS. 14A to 14D illustrate one method where the pouch stoma may be reduced in size by approximating the edges of a portion of the stoma.
Figure 14B:
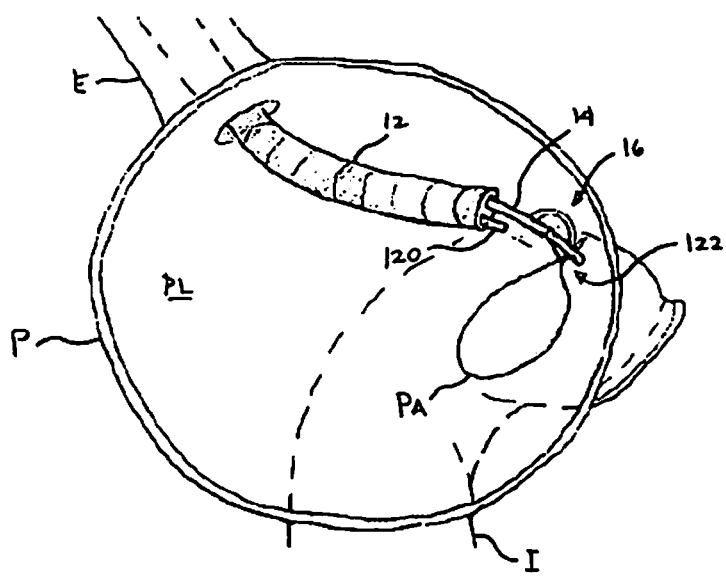

As mentioned above, various combinations of different methods and procedures described herein may be combined with one another as practicable. For example, as shown in FIGS. 14A and 14B, an elongate rigidizable endoscopic body 12 may be advanced per-orally and trans-esophageally into the pouch lumen PL. The distal end of endoscopic body 12 may be directed towards the stoma defined by the pouch anastomosis PA, where flexible body 14 and tissue manipulation assembly 16 may be manipulated to grasp, e.g., the edges 122 of the pouch anastomosis PA, to approximate and secure the tissue, as shown in FIG. 14B. The procedure may be viewed via an imaging assembly, such as fiber optic or CCD or CMOS electronic imager, or endoscope 120.

Figure 14C:
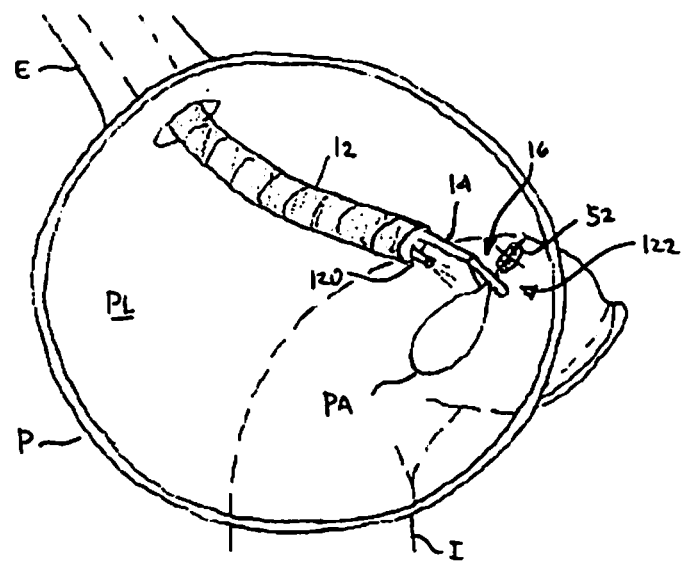
Figure 14D:
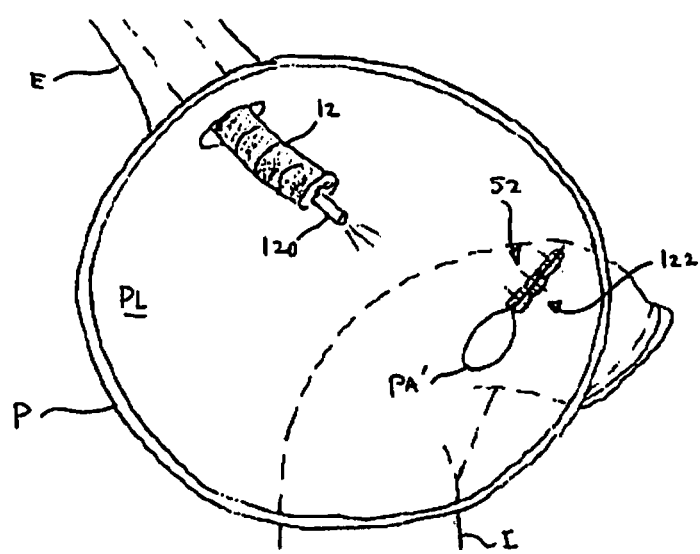
Figure 15A:
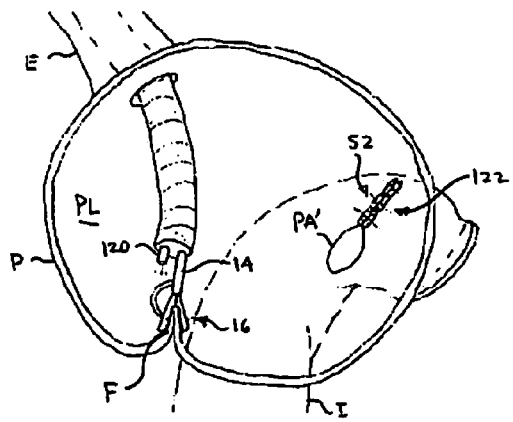
FIGS. 15A to 15C illustrate a combination of various methods where the pouch having a reduced stoma from FIGS. 14A to 14D may be further reduced in pouch size by engaging and securing one or more tissue folds throughout the lumen.

As further shown in FIGS. 14C and 14D, one pair or several pairs of anchors 52 may be deployed into the pouch and/or intestinal tissue to approximate the edges 122 of the pouch anastomosis PA to create a smaller opening through a reduced pouch anastomosis PA'. Once the stoma size has been reduced, the tissue may be viewed via the endoscope 120 and the elongate rigidizable body 12 may be withdrawn from the pouch P. Alternatively and/or optionally, the pouch interior may be further reduced in size by re-directing the elongate body 12 and tissue manipulation assembly 16 to regions around the pouch lumen PL to create and secure with anchors 52 one or more tissue folds F, as shown in FIG. 15A.

Figure 15B:
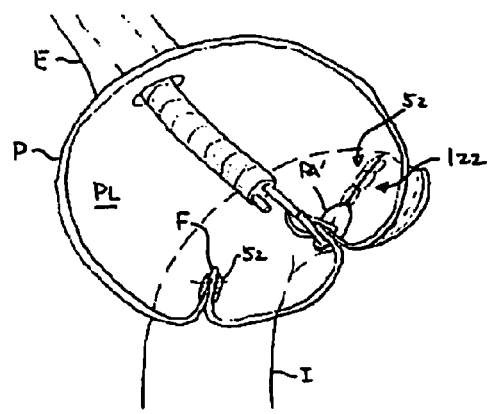
Figure 15C:
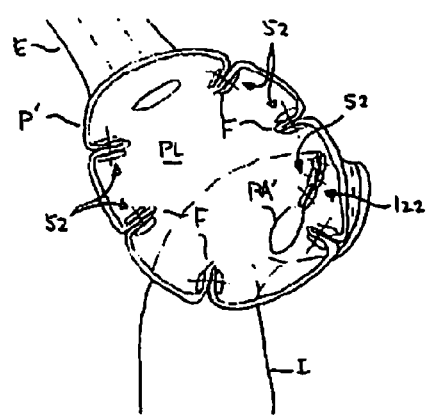

Although at least one tissue fold F may be formed and secured, multiple tissue folds F may be formed and secured around a periphery of the pouch lumen by manipulating the elongate body 12 and tissue manipulation assembly 16, as shown in FIGS. 15B and 15C, to result in a revised pouch P' which not only has a reduced anastomotic opening PA' but also a reduced pouch P' size. The tissue anchors 52 may be deployed in tissue folds F formed randomly throughout the pouch lumen PL or in a circumferential or uniform manner. Furthermore, one or more of the tissue folds and anchors 52 may optionally be interconnected with one another via a drawstring-type mechanism, e.g., a loop suture, made from a suture or biocompatible wire to optionally tighten the tissue folds relative to one another in a purse-string manner. This type of looped suture and anchor assembly allows for the surgeon to manually adjust the size of the restriction opening.

Figure 16A:
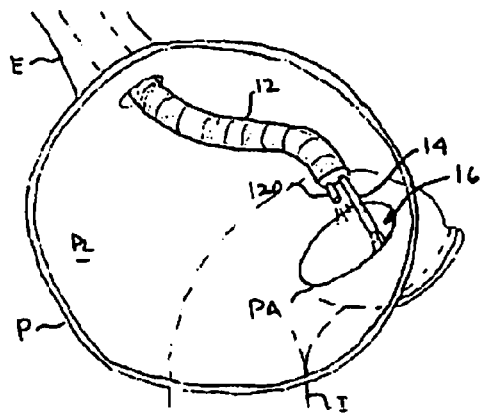
FIGS. 16A to 16C illustrate another method where the pouch stoma may be reduced in size by deploying one or more tissue anchors around a periphery of the stoma.
Figure 16B:
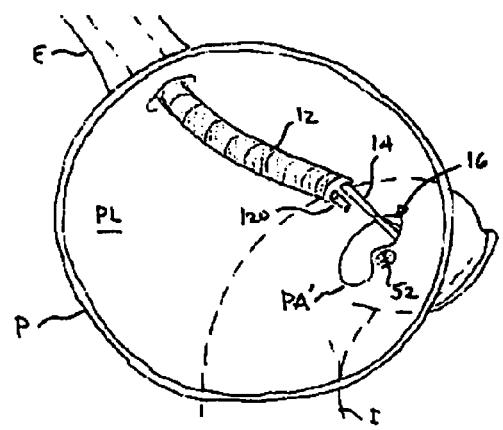
Figure 16C:
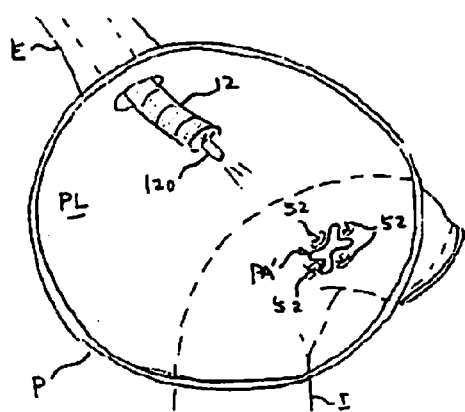
Figure 17A:
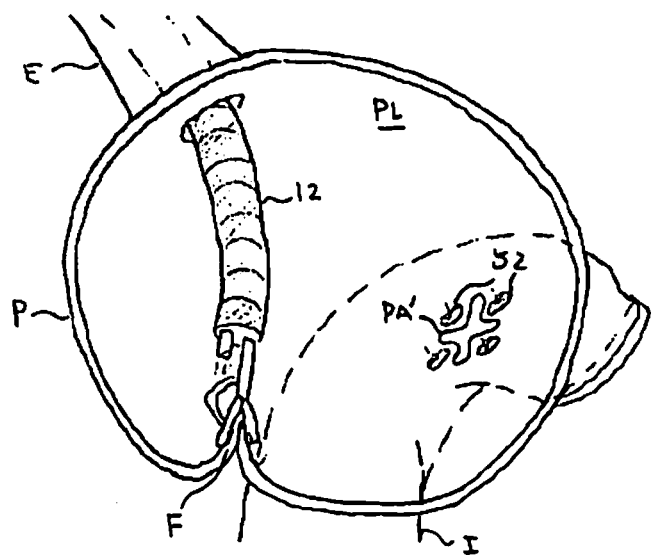
FIGS. 17A and 17B illustrate another combination of various methods where the pouch having a reduced stoma from FIGS. 16A to 16C may be further reduced in pouch size by engaging and securing one or more tissue folds throughout the lumen.
Figure 17B:
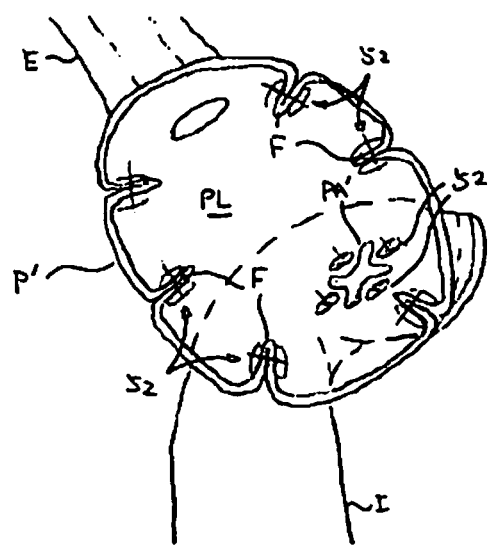

In yet another example for creating a combination of various methods, FIGS. 16A to 16C illustrate the deployment of tissue anchors 52 around a periphery of the pouch anastomosis PA to result in a reduced anastomotic connection PA', as described above. The rigidizable elongate body 12 may be advanced adjacent to the pouch anastomosis PA, as shown in FIG. 16A, where the tissue manipulation assembly 16 may be used to deploy one or more tissue anchor pairs 52 around the pouch anastomosis PA, as shown in FIGS. 16B and 16C. The tissue anchors 52 may be deployed in a radial or circumferential configuration, as described above.

Once the stoma has been reduced in size, the elongate body 12 may optionally be redirected to regions of tissue around the pouch lumen PL to create and secure one or more tissue folds F to result in a reduced pouch P' also having a reduced pouch anastomosis PA'. As described above, the tissue folds F may be formed uniformly or randomly through the pouch lumen PL and may be further interconnected, as desired.

These examples are intended to illustrate the various types of procedures and methods which may be combined as practicable and are not intended to be limiting in any way. Moreover, the elongate body 12 may be transitioned between a rigid state and a flexible state at any time during a procedure depending upon the desired degree of platform stability during tissue manipulation and securement within the pouch lumen PL.

Although various illustrative embodiments are described above, it will be evident to one skilled in the art that a variety of combinations of aspects of different variations, changes, and modifications are within the scope of the invention. It is intended in the appended claims to cover all such changes and modifications that fall within the true spirit and scope of the invention.

The invention claimed is:

1. A method of surgery, comprising:
advancing a distal end of an endoscopic flexible body per-orally into a pouch lumen PL of a stomach of a patient;
directing the distal end of the endoscopic flexible body towards a stoma defined by a pouch anastomosis PA;
advancing a tissue engagement member from the distal end of the endoscopic flexible body and engaging tissue at a first position adjacent to a first edge of the pouch anastomosis PA;
manipulating a tissue manipulation assembly having a first jaw attached to a pivotal coupling on a tubular body, and a second jaw pivotally attached to the first jaw, including advancing a launch tube to pivot the second jaw towards the first jaw;
grasping the tissue at the first position between the first jaw and the second jaw;
moving a needle assembly through the launch tube and through the grasped tissue at the first position;
deploying a first tissue anchor from the needle assembly through the grasped tissue at the first position;
grasping tissue at a second position adjacent to a second edge of the pouch anastomosis PA between the first jaw and the second jaw;
moving the needle assembly through the launch tube and through the grasped tissue at the second position;
deploying a second tissue anchor from the needle assembly through the grasped tissue at the second position; and
moving the first tissue anchor towards the second tissue anchor to make the pouch anastomosis PA smaller.

2. The method of claim 1 further including engaging the tissue at the first position with a tissue engagement member of the endoscopic flexible body and pulling the engaged tissue, before grasping the tissue at the first position between the first jaw and the second jaw.

3. The method of claim 1 further including deploying third and fourth tissue anchors into intestinal tissue at the pouch anastomosis PA to approximate the edges of the pouch anastomosis PA.

4. The method of claim 3 further including deploying fifth and sixth tissue anchors into intestinal tissue at the pouch anastomosis PA to approximate the edges of the pouch anastomosis PA.

5. The method of claim 3 further including interconnecting two or more of the tissue anchors via a drawstring.

6. The method of claim 1 further including reducing the size of the pouch lumen PL by re-directing the tissue manipulation assembly to regions around the pouch lumen PL to create one or more tissue folds F and securing the tissue folds F with additional anchors.

7. The method of claim 1 further including deploying additional tissue anchors to maintain tissue folds F formed in a circumferential or uniform manner.

8. The method of claim 1 further including deploying additional tissue anchors to maintain tissue folds F and interconnecting one or more of the additional tissue anchors via a drawstring.

9. The method of claim 8 with the drawstring comprising a loop suture made from a suture or biocompatible wire to tighten the tissue folds F in a purse-string manner.

10. The method of claim 9 further including manually adjusting a dimension of the pouch anastomosis PA.

11. The method of claim 1 further including deploying additional tissue anchors in a radial or circumferential configuration.

12. The method of claim 1 wherein the tissue manipulation assembly on the endoscopic flexible body is separate from the tissue engagement member.

13. The method of claim 1 further comprising rotating a helix on the tissue engagement member into the tissue at the first position.

14. A method of surgery comprising:
advancing a distal end of an endoscopic flexible body per-orally into a pouch lumen PL of a stomach of a patient;
directing the distal end of the endoscopic body to a pouch anastomosis PA;
engaging tissue at a first position of the pouch anastomosis PA with a tissue engagement member of the endoscopic flexible body;
grasping tissue at the first position between a first jaw and a second jaw of a tissue manipulation assembly by advancing a launch tube attached to the second jaw and not attached to the first jaw;
moving a needle assembly through the launch tube and through the grasped tissue at the first position;
deploying a first tissue anchor from the needle assembly at the first position;
grasping tissue at a second position of the pouch anastomosis PA between the first jaw and the second jaw;
moving the needle assembly through the launch tube and through the grasped tissue at the second position;
deploying a second tissue anchor from the needle assembly at the second position; and
deploying third and fourth tissue anchors into intestinal tissue at the pouch anastomosis PA; and
moving two or more of the tissue anchors towards each other via a drawstring to make the pouch anastomosis PA smaller.

15. The method of claim 14 wherein the first jaw is pivotally attached to the endoscopic flexible body and the second jaw is pivotally attached to the first jaw.

16. The method of claim 14 wherein the tissue manipulation assembly on the endoscopic flexible body is separate from the tissue engagement member.

17. The method of claim 14 further comprising rotating a helix on the tissue engagement member into the tissue at the first position.

18. The method of claim 14 comprising grasping the tissue at the first position by advancing the launch tube to pivot the second jaw towards the first jaw, with the first jaw attached to a pivotal coupling on a tubular body of the tissue manipulation assembly, and with the second jaw pivotally attached to the first jaw.

* * * * *